United States Patent
Habib

(10) Patent No.: US 11,202,672 B2
(45) Date of Patent: Dec. 21, 2021

(54) METHODS AND SYSTEMS FOR RESTORING PATENCY

(71) Applicant: EMCISION LIMITED, Hertfordshire (GB)

(72) Inventor: Nagy Habib, London (GB)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 694 days.

(21) Appl. No.: 16/001,505

(22) Filed: Jun. 6, 2018

(65) Prior Publication Data

US 2018/0344394 A1 Dec. 6, 2018

Related U.S. Application Data

(63) Continuation of application No. 13/019,911, filed on Feb. 2, 2011, now abandoned.
(Continued)

(51) Int. Cl.
*A61B 18/14* (2006.01)
*A61B 17/00* (2006.01)
(Continued)

(52) U.S. Cl.
CPC ..... *A61B 18/1492* (2013.01); *A61B 2017/00084* (2013.01); *A61B 2017/22001* (2013.01); *A61B 2017/22038* (2013.01); *A61B 2018/00422* (2013.01); *A61B 2018/00702* (2013.01); *A61B 2018/00875* (2013.01)

(58) Field of Classification Search
CPC .. A61B 2018/00535; A61B 2018/0022; A61B 2018/00404; A61B 2018/00482; A61B 2018/126; A61B 2018/00214; A61B 18/12
See application file for complete search history.

(56) References Cited

U.S. PATENT DOCUMENTS

| | | | | |
|---|---|---|---|---|
| 4,998,933 A | * | 3/1991 | Eggers | A61B 18/1492 604/114 |
| 5,254,121 A | * | 10/1993 | Manevitz | A61B 17/22022 606/108 |

(Continued)

*Primary Examiner* — Ronald Hupczey, Jr.
(74) *Attorney, Agent, or Firm* — Kacvinsky Daisak Bluni PLLC

(57) ABSTRACT

A method for maintaining patency in a duct or hollow vessel located within the body of a patient is described wherein the duct includes one or more obstructions. The method comprises the steps of introducing a device into the duct, the device comprising a catheter having a distal and a proximal end, wherein the distal end includes a distal tip portion and wherein the distal tip portion comprises at least one energy delivery member; locating the device within the duct at a position proximal to the obstruction; delivering energy to the duct and any surrounding tissue via the at least one energy delivery member for a specified time period, so that the obstruction is removed from the duct; and withdrawing the device from the duct. It is optional to subsequently place a device such as a stent at the therapy site in order to further maintain long term patency of the duct. It is also optional to apply a dilation force to the duct or hollow vessel after the energy delivery phase. Systems are also described for performing the methods of the disclosure.

18 Claims, 6 Drawing Sheets

Related U.S. Application Data

(60) Provisional application No. 61/301,994, filed on Feb. 5, 2010, provisional application No. 61/302,434, filed on Feb. 8, 2010.

(51) Int. Cl.
*A61B 17/22* (2006.01)
*A61B 18/00* (2006.01)

(56) References Cited

U.S. PATENT DOCUMENTS

| | | | | |
|---|---|---|---|---|
| 5,419,767 | A * | 5/1995 | Eggers | A61B 18/149 604/114 |
| 5,749,914 | A * | 5/1998 | Janssen | A61B 18/12 607/116 |
| 6,317,615 | B1 * | 11/2001 | Knight | A61B 18/1492 600/372 |
| 6,582,423 | B1 * | 6/2003 | Thapliyal | A61B 18/1206 128/898 |
| 8,066,702 | B2 * | 11/2011 | Rittman, III | A61M 25/007 606/41 |
| 8,401,667 | B2 * | 3/2013 | Gustus | A61F 7/123 607/99 |
| 2008/0188912 | A1 * | 8/2008 | Stone | A61F 7/12 607/99 |

* cited by examiner (a)

(b)

(c)

(d)

METHODS AND SYSTEMS FOR RESTORING PATENCY

RELATED APPLICATION

This application is a continuation of U.S. patent application Ser. No. 13/019,911, filed Feb. 2, 2011, which claims the full Paris Convention benefit of and priority to U.S. Provisional Patent Application Ser. No. 61/302,434, filed Feb. 8, 2010, and U.S. Provisional Patent Application Ser. No. 61/301,994, filed Feb. 5, 2010, the contents of which are incorporated by reference herein in their entirety, as if fully set forth herein.

FIELD

The disclosure relates to methods for restoring patency in a duct or hollow vessel located within the body of a patient.

BACKGROUND

As many as 90% of patients who present with pancreatic adenocarcinoma or extrahepatic cholangiocarcinoma will have surgically unresectable disease, either because of local vascular involvement or metastatic disease. Life expectancy in patients with unresectable disease is poor, with a median survival of six to eight months. Most of these patients will experience biliary obstruction and jaundice. The priority in the management of such patients is to effectively and durably relieve the jaundice. By relieving jaundice the patient feels better, quality of life is improved and if appropriate facilitates chemotherapy. Malignant biliary obstruction is relieved either by deploying a stent through endoscopic retrograde cholangiography (ERC) or percutaneous transhepatic cholangiography (PTC). In most cases a self-expanding mesh metal stent (SEMS) is used which has a longer patency than a plastic stent.

Despite using SEMS patients often continue to have problems with stent occlusion produced from tumor ingrowth. From a technical perspective this can be a difficult problem to treat requiring in hospital management and repeated biliary interventions.

Deployment of radiofrequency (RF) energy via a catheter or endoscope has been used in the past in order to destroy or ablate tissue. U.S. Pat. No. 6,066,139 describes an apparatus comprising a bipolar RF catheter for use in creating thermal lesions for the purpose of sealing or ligating vessels such as fallopian tubes or embolizing blood vessels. The apparatus described in U.S. Pat. No. 6,066,139 administers RF energy to heat surrounding tissue to a temperature of between 95.degree. C. and 105.degree. C. (203.degree. F. to 221.degree. F.) in order to cause necrosis of the tissue and collapse of the duct or vessel. RF energy has also been applied for the purpose of bile duct ablation as described in WO-03/053,267. Hence, whilst the use of RF energy to ablate or induce closure of vessels within the body is known, use of controlled energy delivery to maintain or restore patency in an already obstructed vessel or duct has not been considered previously.

There is a need to provide additional methods for treating problems such as stent occlusion caused by tumor ingrowth, and restoration of patency in ducts or vessels obstructed by tissue or other material.

DESCRIPTION

To improve the patency of obstructed ducts, such as by malignant tumor obstruction, the present inventors have developed a radiofrequency (RF) catheter that can be inserted over a guidewire with the aim that controlled application of RF energy can be used to ablate a luminal tumor or other occlusion and optionally prior to insertion of a stent, such as a SEMS. The clinical use of RF has an established role in the ablation of cancers in solid organs such as the liver. However, the use of RF to maintain patency in ducts such as those of the biliary system has not been disclosed before.

Accordingly, in a first aspect the disclosure provides a method for maintaining patency in a duct located within the body of a patient, wherein the duct includes one or more obstructions, the method comprising the steps of:

(a) introducing a device into the duct, the device comprising a catheter having a distal and a proximal end, wherein the distal end includes a distal tip portion and wherein the distal tip portion comprises at least one energy delivery member;

(b) locating the device within the duct at a position proximal to the obstruction;

(c) delivering energy to the duct and any surrounding tissue via the at least one energy delivery member for a specified time period, so that patency is restored to the duct; and (d) withdrawing the device from the duct.

In a specific embodiment, the method of the disclosure may further comprise the additional step of:

(e) inserting a stent into the duct at the location proximal to the obstruction where the energy was delivered so as to maintain patency in the duct.

Suitable stents may be selected from SEMS or plastic stents.

In some exemplary implementations there may be an additional step of:

(e) applying a dilation force to the duct so as to maintain patency.

In such exemplary implementations the dilation force may be applied by insertion of a second device into the duct that comprises one or more expandable members that are able to apply radial force on the walls of the duct. Suitably the second device is a balloon dilation catheter. Optionally the device comprises an expandable mesh structure such as a tethered self expanding stent.

In some exemplary implementations the method of the disclosure can be used where the position proximal to the obstruction already comprises a pre-located stent that has become obstructed subsequent to prior placement in the duct. In some exemplary implementations a system for restoring full or partial patency by increasing the luminal diameter of a duct that has been subject to full or partial occlusion, in a patient in need thereof. The system comprises: a first device that comprises an endoscope, the endoscope comprising at least one central lumen extending along its length; a second device that comprises a catheter, the catheter having a distal terminus and a region proximal to the distal terminus defining a distal tip region, the distal tip region comprising at least one or more RF electrodes; and a third device that comprises a SEMS delivery catheter;

wherein the central lumen of the first device is configured so as to be of a diameter that is able to accommodate the second and third devices consecutively. Typically the central lumen will be in the form of a biopsy channel. In specific embodiments of the invention the second device may comprise a central lumen also, in order that it can be placed over a prelocated guidewire.

Some exemplary implementations of the disclosure relate to removal or displacement of obstructions from ducts within the pancreatic and biliary networks. These examples are not intended to be a limitation on the use.

DRAWINGS

The above-mentioned features and objects of the present disclosure will become more apparent with reference to the following description taken in conjunction with the accompanying drawings wherein like reference numerals denote like elements and in which:

FIG. 1 shows a close up photograph of the distal end of a bipolar RF device suitable for use in the present disclosure showing two ring electrodes (A and B) which are spaced 8 mm apart and the most distal electrode (marked A) is 5 mm from the distal terminus of the catheter. The line C shows the approximate length of the RF ablation zone (around 25 mm) generated in a cylindrical region coaxial to the electrodes.

FIG. 2 shows a microscopy image of a Haematoxylin and Eosin stained resected common bile duct, demonstrating a mild thermal injury. In the common bile duct there is erosion with patchy denudation of the epithelium. Underlying glands show some dilatation and focal inflammation but no necrosis.

FIG. 3 shows a microscopy image of a Haematoxylin and Eosin stained resected common bile duct, demonstrating a moderate thermal injury. Complete burn with no residual epithelium. Subepithelial cleft-like spaces filled with blood cells.

FIG. 4 shows a photograph of a laparotomy in which a heating effect on the outer surface of tissue surrounding the bile duct and extending into pancreas was observed. Tip of forceps pointing to area of coagulative necroses outside target area. The RF device had been activated at 20 Watts for 1 minute.

FIGS. 7(a) to (d) show a series X-ray photographs (via endoscopic retrograde cholangiopancreatography (ERCP)) of the endoscopic insertion and administration of RF energy to restore patency in a blocked bile duct in a mammalian system. (a) the position of the obstruction in the CBD is shown by the white arrow. (b) the position of the distal electrode on the RF catheter is indicated by the white arrow.

FURTHER DESCRIPTION

Prior to setting forth the invention, a number of definitions are provided that will assist in the understanding of the disclosure. All references cited herein are incorporated by reference in their entirety. Unless otherwise defined, all technical and scientific terms used herein have the same meaning as commonly understood by one of ordinary skill in the art to which this disclosure belongs.

Figure 6:
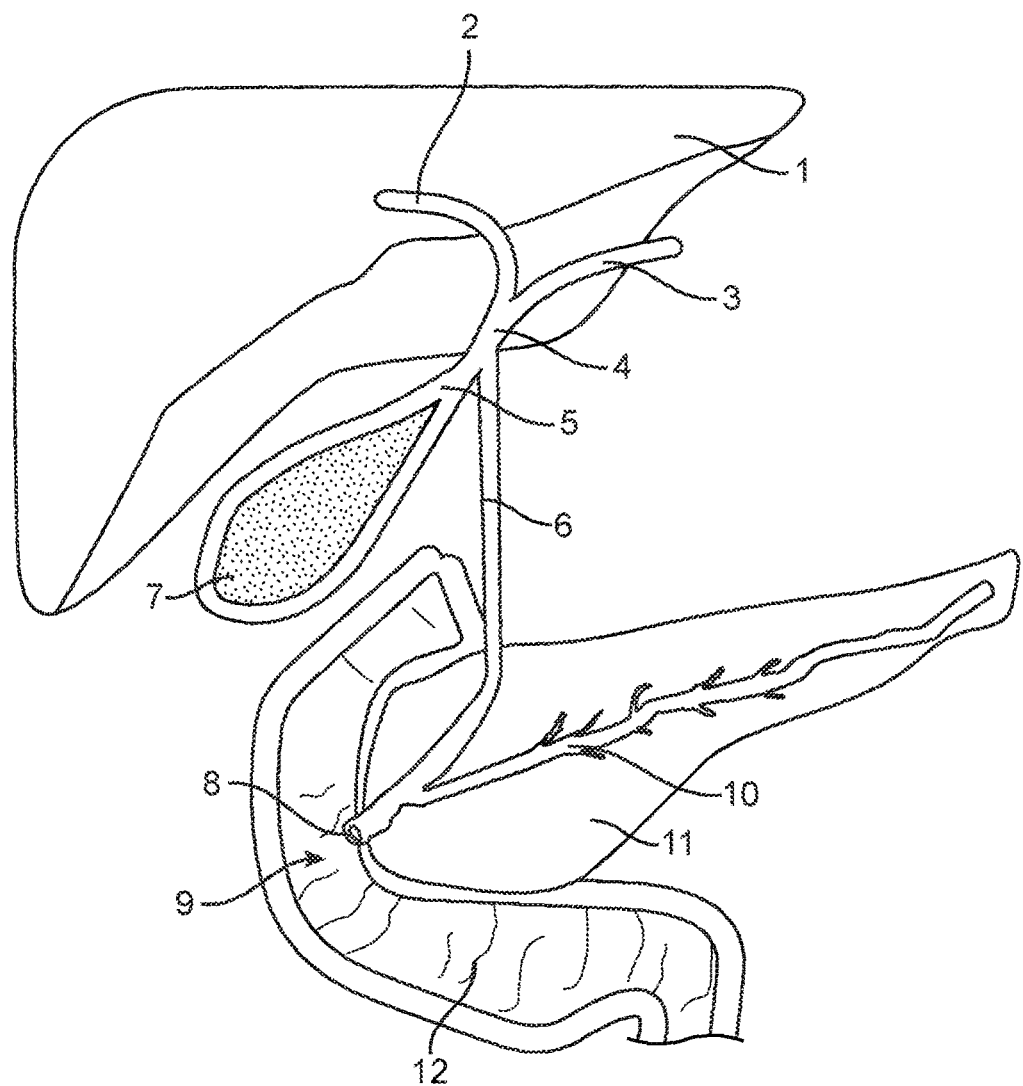
FIG. 6 shows a diagram of the biliary tree in humans comprising the various constituent ducts and also the surrounding organs: (1) liver, (2) right hepatic duct, (3) left hepatic duct, (4) common hepatic duct, (5) cystic duct, (6) common bile duct, (7) gall bladder, (8) sphincter of Oddi, (9) ampulla of Vater, (10) pancreatic duct, (11) pancreas, and (12) duodenum.

The term "duct" is used herein to denote a hollow vessel or channel located within the body of a patient. Typically, ducts may lead to or from an organ and may be involved in the transport of endocrine or other secretions within the body. In accordance with the present disclosure, ducts do not typically include blood-carrying vessels such as veins, arteries or arterioles, but may include vessels of the lymphatic system. Ducts that are suitably treated in accordance with the methods of the present disclosure may be selected from the ducts and channels that comprise part of the biliary system, including the common bile duct (CBD), the pancreatic duct, the cystic duct, the right and left hepatic ducts and the common hepatic duct (see FIG. 6). Other ducts may include fallopian tubes; channels within the respiratory system, such as bronchioles; channels within the gastrointestinal tract, including the oesophagus; and channels that are a part of the urinary tract, including the ureters and the urethra, including for the treatment of benign or malignant prostatic disorders. The method of the disclosure can also be applied in the ventricular system for relief of fluid build up in conditions such as hydrocephalus.

The term "obstruction" is used herein to denote an accumulation of matter, or tissue that partially or completely blocks the duct so as to affect normal patency of the duct. Typically obstructions are caused by a benign or malignant tumor present in tissue within the duct or in tissue adjacent to the duct—thereby causing obstruction by means of compression of the duct. Alternative obstructions can result by an accumulation granulation tissue (scar tissue) as a result of prior trauma, such as injury or surgery, or a pathological condition (for example, endometriosis or infection). Obstructions caused by scar tissue can sometimes result in a stricture of the duct, thereby leading to a blockage. A further obstruction my result from formation of a blood clot (thrombosis) within the duct, possibly following traumatic injury or acute infection.

The term "patency" is used herein to denote the level of the openness (lack of obstruction) of a bodily passage or duct. A fully patent duct is one that is functioning normally with no significant obstruction. A semi-occluded duct may be regarded as functionally patent in spite of partial obstruction, whereas an obstructed duct would generally be considered to be non-patent. The method of the present disclosure is suitable for use in situations where restoration to full or at least partial patency is required in a duct that is blocked or functionally occluded. Restoration to full or at least partial patency in ducts such as the common bile duct is sufficient in many cases to relieve symptoms of jaundice and/or pancreatitis in patients with hepatic or pancreatic tumors.

Figure 1:
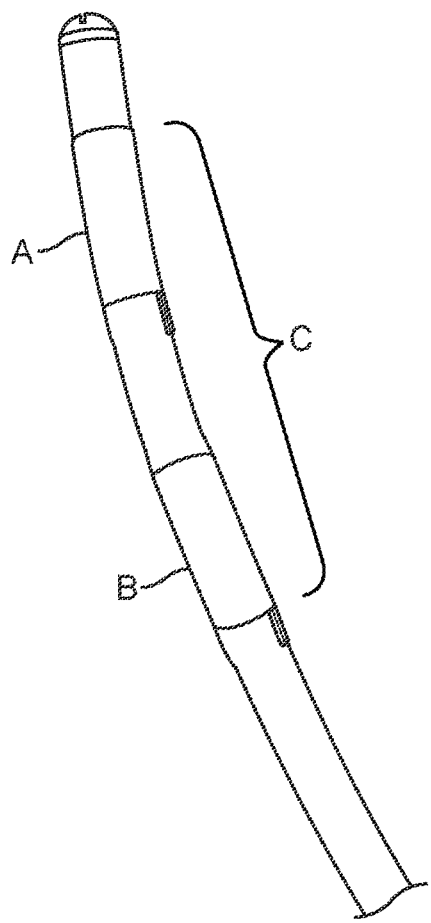

Suitable devices that can be used in the method of the disclosure are catheters, probes, endoscopes or guidewires that comprise the ability to provide topical delivery of energy at a specified location within the body of a patient. The use of radiofrequency energy is exemplified in the examples set out in detail below, however it is understood that alternative energy delivery systems, such as ultrasound, microwave, electrical or laser energy could be employed in the method of the disclosure. RF devices that may be used according to the methods of the disclosure are described in the inventor's co-pending International Patent applications WO-A-2007/135,431 and WO-A-2008/084,239 the contents of which are incorporated herein by reference. A specific implementation of the disclosure utilizes a catheter that comprises one or more radiofrequency (RF) electrodes at the distal tip. In a particular embodiment of the disclosure, the energy delivery member comprises at least two RF electrodes arranged in a bipolar configuration (see FIG. 1). As shown in FIG. 1, in some implementations two RF electrodes can be longitudinally spaced apart by a distance along the central axis of the distal tip of the catheter. The distal tip can terminate in a smooth, conical or hemispherical cap to ease insertion into the hollow anatomical structure. Typically, the at least two RF electrodes are spaced no less than about 1 mm and no more than about 15 mm apart; optionally no less than about 2 mm and no more than about 12 mm apart; suitably between about 3 mm and about 10 mm apart. In one embodiment of the disclosure, the at least two RF electrodes are spaced about 8 mm apart.

In some exemplary implementations optimal spacing of RF electrodes allows for the delivery of energy in a substantially cylindrical region coaxial to the distal tip of the device and extending between and about the at least two electrodes. An advantage of this arrangement is that the energy is dissipated over a larger area, thereby reducing the formation of localized hotspots (foci) that can lead to excessive thermal damage of surrounding healthy tissue. In some exemplary implementations the bipolar electrode arrangement is such that the most distal electrode is not located at the leading edge (distal terminus) of the device, but rather about 5 mm behind the distal terminus. This arrangement helps to prevent collapse of the duct during the thermal ablation phase.

A specific embodiment of the present disclosure provides for controlled delivery of energy to the site of therapy—i.e. the location in the duct where a blockage has occurred. Controlled release of energy is sufficient to induce ablation and remodelling of tissue or material that is responsible for the obstruction, but not so much as to induce extreme tissue damage that would result in collapse of the duct (permanent obstruction) or organ failure. In one particular embodiment of the disclosure the level of energy (power) applied to the obstruction via the device is no more than about 10 Watts (10 W), typically no less than 1 W and up to 8 W, more suitably around 6 W or 7 W. The total energy applied to the treatment site will vary from patient to patient, however, in an example of the disclosure in use the total energy applied in procedures to restore patency to occluded biliary ducts was no less than 1200 Joules and up to 3600 Joules in the procedure as a whole. It will be appreciated that for more minor blockages lower amounts of total energy will be sufficient to restore patency, whereas for more acute strictures a greater amount of energy will be required.

Energy will be applied at the site of treatment in one or more discrete time periods of administration. The time period for administration of energy to the therapy site (proximal to the obstruction) is usually for no less than about 10 and no more than about 300 seconds and suitably no less than about 30 and no more than about 200 seconds. In examples described in more detail below the specified time of energy delivery is set at around 2 minutes (120 seconds). However, it will be understood by the skilled person that this time may vary depending upon the nature of the obstruction (thrombus, stricture or tumor), the location of the duct within the body (particularly with respect to significant local anatomy) and also the power rating of the device being used in the method. In some exemplary implementations restoration of patency to an occluded common bile duct may require several applications of energy with intervals of rest periods to allow the ablated tissue to cool so as to avoid unnecessary heating of surrounding tissues. Rest periods may suitably range from at least 1 second to at most 2 or 3 minutes, although typically a rest interval might be around one minute in length. In this way removal of the occluding mass and the corresponding increase in lumenal diameter is achieved by sequential applications of energy along the length of a stricture within the compromised duct or vessel.

To assist with the control of energy delivery, devices used in the method of the invention may further comprise a sensor for measuring impedance in the tissue whilst energy is delivered to the duct and surrounding tissues in the energy delivery step. Observing the level of electrical impedance in the surrounding tissue is one way of monitoring the progress of the therapy/heating phase. For instance, electrical impedance can be monitored during heating and when a predefined threshold is reached the heating phase is deemed to have been completed. Likewise, the device can further comprise a temperature sensor within the distal tip portion.

In some exemplary implementations described in more detail below, a method is provided of using endoscopically applied radiofrequency treatment prior to insertion of a self expanding metal stent (SEMS) in an un-resectable malignant bile duct obstruction. At present, the use of SEMS is the standard technique to ensure continued biliary drainage in patients with life expectancy beyond 3 months. However, up to 50% of patients with SEMS will re-present with stent occlusion within the first 6-8 months, this often leads to significant morbidity and mortality as well as delays in chemotherapy regimes. The present disclosure allows for restoration of patency through minimally invasive procedures thereby allowing for amelioration of the symptoms of bile duct obstruction.

SEMS are typically open-ended cylinders constructed from a metal wire mesh, including shape memory alloys such as nitinol and platinum coated nitinol. The SEMS are designed to resist radial compression when in the expanded state and conform easily to the anatomy of the vessel or duct in which they have been deployed. In this way the SEMS will support the duct and resist collapse following thermal ablation treatment according to the methods of the present invention. Exemplary SEMS suitable for use in the methods and systems of the invention include Zilver® brand biliary SEMS (Wilson-Cook Medical, Inc., NC, USA) or Wallstent® SEMS (Boston Scientific, Inc., MA, USA).

Figure 7:
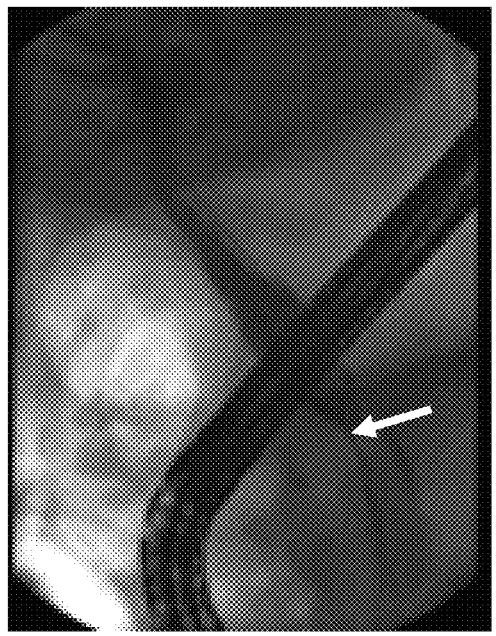
Figure 7:
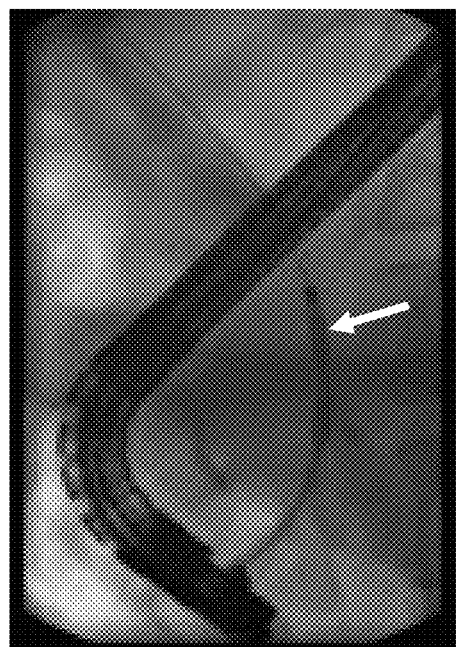
Figure 7:
Figure 7:

In accordance with a specific embodiment of the disclosure a typical procedure may involve the following steps:

(1) a suitable endoscope is inserted into or proximate to the occluded duct; the endoscope will comprise a channel of a size suitable to accommodate and facilitate deployment of a catheter that includes a bipolar RF electrode energy delivery module at its distal tip (see FIG. 7(a));

(2) the endoscope and/or the catheter will be advanced to a position within the duct that is proximate to the site of full or partial obstruction (which may or may not include a pre-located stent); this may be facilitated by the use of a guidewire as well as ECRP or other suitable imaging techniques;

(3) when the catheter tip is located at the correct position, RF energy is applied at a power level and for one or more specified time periods to induce ablation of the obstruction but not widespread necrosis or significant damage of the duct that would result in permanent occlusion (see FIG. 7(b));

(4) the catheter can be withdrawn from the treatment site when patency is established (via X-ray fluoroscopy, for example) and if necessary applied to one or more additional obstructions (see FIG. 7(c));

(5) in an optional additional step, a SEMS is inserted into the location where therapy has been applied in order to maintain patency for a longer period of time (see FIG. 7(d)). Further SEMS may be inserted proximate to the first inserted SEMS in order to maintain a patent tract of the duct.

In certain circumstances it may not be clinically necessary or appropriate to insert a stent, such as a SEMS, into the duct. In such cases it may, nevertheless, be desirable to apply a radial expansive force to the duct in order to further assist the effects thermal ablation. Application of an expansive force to the duct can be achieved by methods known to the skilled person, and may include subsequent deployment of a balloon catheter dilator or equivalent, or use of a tethered expanding stent that is removed from the vessel immediately following the application of the expansive force. Suitable devices for administering an expansive force to the duct under treatment may include use of a wireguided balloon dilator, such as the CRE™ Wireguided Ballon Dilator, Extractor™ RX Retrival Balloon system or Gateway™ PTA Balloon Catheter (Boston Scientific, MA, USA). Typically balloon dilators will comprise a catheter-type elongated body which further comprises a one of more extended bladders (or balloons) at the distal end of the device. The bladders may be inflated by injection of a fluid (such as saline) into a chamber comprised within the bladder, thereby exerting a dilatory or radially expansive force on tissue surrounding the bladder when placed within a vessel or duct. The dilation radius and force can be controlled by the user of the device, so as to avoid risk of rupture of the duct or vessel.

In some exemplary implementations a system for restoring full or partial patency by increasing the luminal diameter of a duct that has been subject to full or partial occlusion, in a patient in need thereof. The system comprises:

(i) a first device that comprises an endoscope, the endoscope comprising at least one central lumen extending along its length;

(ii) a second device that comprises a catheter, the catheter having a distal terminus and a region proximal to the distal terminus defining a distal tip region, the distal tip region comprising at least one or more RF electrodes; and (iii) a third device that comprises a stent delivery catheter and a stent that is to be delivered by the stent delivery catheter;

wherein the central lumen of the first device is configured so as to be of a diameter that is able to accommodate the second and third devices consecutively.

Such systems, or aspects thereof, may comprise a standard endoscope with optical or ultrasound guidance features, that further comprises a central lumen or channel—such as a biopsy channel—that is able to accommodate the second or third devices. The endoscope is used to locate the site of duct occlusion (e.g. stricture), at which point an optional standard guide wire can be inserted into the central lumen and over which the RF catheter is advanced to a location proximate to the site of the blockage. The RF catheter is deployed and ablation energy is applied to the occluded region in accordance with the methods disclosed herein. Once a satisfactory level of patency is achieved the second device is removed from the first device and the third device is advanced to the site of treatment—over the guide wire if one is present—to allow for deployment of a SEMS. In some cases more than one SEMS may be required at the treatment site, hence, systems may include a plurality of third devices.

It will be appreciated by on of ordinary skill in the art that the methods and systems of the disclosure are not limited to use solely in the biliary system and that other ducts or hollow anatomical structures may be subject to equivalent treatment where occlusion or other pathological malformation is present. In an exemplary implementation the system, or aspects thereof, described above is utilized in the treatment of gastro-esophageal varices. By way of non-limiting example, occlusions in the esophagus caused by varices (particularly in cases of liver cirrhosis) can be treated in a manner as described herein as mentioned for other ducts in the body. Likewise, gastric varices in usually inaccessible locations, such as the fundus of the stomach, are also suited for treatment according to the methods and systems disclosed herein.

Benign or malignant prostatic conditions, including prostate cancer and benign prostate hyperplasia (BPA), are also suitable for treatment via the methods and systems of the present invention. Restoration of patency to the urethra can be facilitated via energy ablation treatment (such as via RF) in conjunction with balloon dilation and/or placement of a stent.

The disclosure is further illustrated by the following non-limiting examples.

EXAMPLES

Description of Device

The CE marked endoscopic bipolar RF catheter developed and used in the present examples is called EndoHPB (EMcision Ltd, UK). EndoHPB was developed by a collaboration between engineers at Imperial College, University of London and EMcision Ltd, UK. EMcision Ltd is a company developed out of Imperial College.

EndoHPB is a single use bipolar radiofrequency catheter. It is an 8 French (2.7 mm), 1.8 m long nylon tube and is designed to be used either at PTC or ERC over a 0.035 inch (0.9 mm) guidewire. If used percutaneously a 10 French (3.3 mm) bore introducer is required. The outer body of EndoHPB is made of braided pebax 7033, the inner body of polyimide with a PTFE lining to provide smooth tracking. At the tip of the device are two stainless steel ring electrodes spaced 8 mm apart, with the distal electrode 5 mm from the tip of the device (see FIG. 1). The heating zone length produced is 25 mm+/−3 mm. EndoHPB can be used with approved radiofrequency generators. For the present examples the RITA™ 1500×RF (Angiodynamics, Queensbury, N.Y.) generator was used, although the Cosman Coagulator CC-1 (Radionics, Burlington, Mass.) is also suitable.

Example 1

Animal Model

A porcine model was used. Three animals in total were used. The animals were fasted overnight and allowed free access to water. They were sedated with an intramuscular injection of 5 mg/kg azaperone and 10 mg/kg ketamine. In order to reduce salivary and bronchial secretions atropine at a dose of 0.05 mg/kg was administered intramuscularly. Anaesthesia was induced with propofol (2.5-3.5 mg/kg), infused via the auricular vein. All the pigs were orally intubated and mechanically ventilated (Hallowell-EMC 2000). Tidal volume was maintained at 10-15 ml/kg, and the respiratory rate at 14-16 breaths/min. Anaesthesia was maintained with sevoflurane, administered at 1-1.5 MAC concentration (2.5-3.75%), in a closed circle system (MDS Matrx, VMS). Finally, buprenorphine (0.005-0.02 mg/kg intravenously) was administered for analgesia.

Interventional Procedure

A Pentax™ side viewing endoscope (ED3440T) was used. The orifice of the common bile duct was identified and enlarged using cutting forceps. Under fluoroscopic control a 0.035" 260 cm hydra jagwire (Boston Scientific) was inserted into the duct. EndoHPB was then inserted over the guidewire and connected to a RITA™ 1500×RF generator. EndoHPB was then activated for different time intervals and wattages along the bile duct. On completion of the experiment, the animal was killed. Laparotomy was performed to see if there was any evidence of thermal injury and to allow the common bile duct to be resected for histology.

Results

Figure 2:
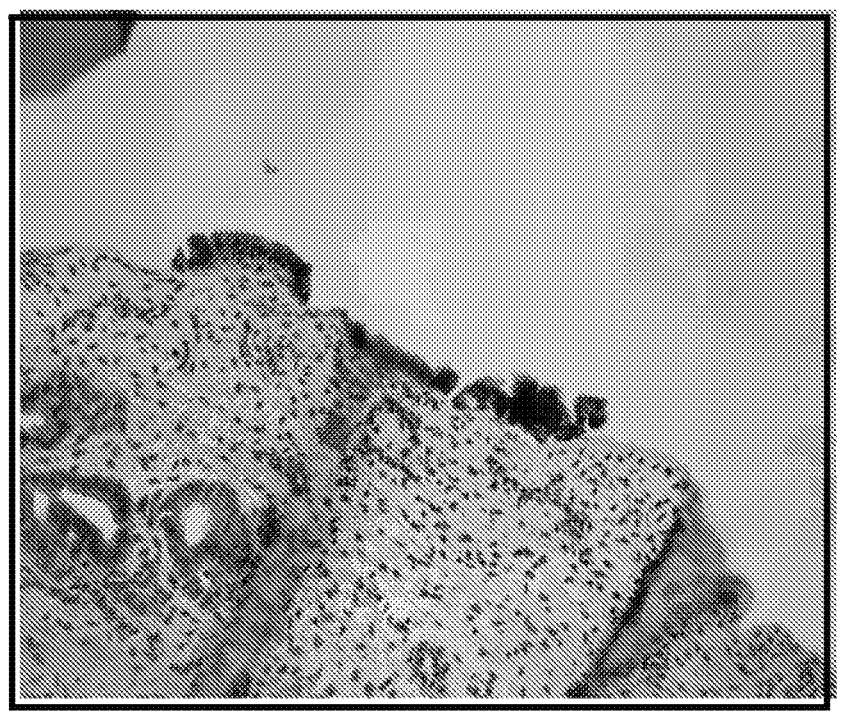
Figure 3:
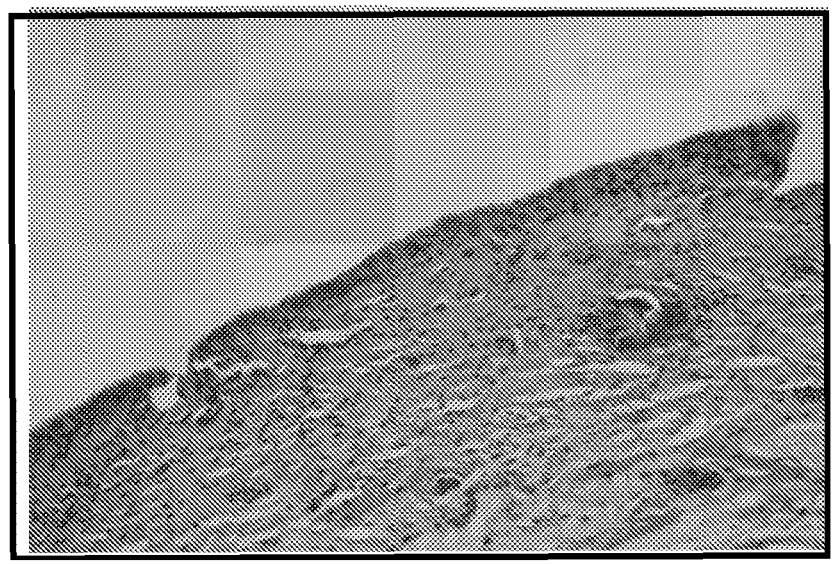
Figure 4:
Figure 5:
FIG. 5 shows a microscopy image of a Haematoxylin and Eosin stained resected common bile duct, demonstrating severe thermal injury. Significant thermal changes with extensive coagulative necrosis of the wall are found.

Use of EndoHPB was found to be compatible with the Pentax™ side viewing endoscope (ED3440T) and could be operated easily via the 3.2 mm biopsy channel. In the porcine model the common bile duct was found to be short and more difficult to cannulate at ERC so EndoHPB was only tested at two different levels within the bile duct of each animal. Table 1 summarises the power and time settings of EndoHPB used in each pig, and the amount of thermal injury observed on histological criteria. On the lower power settings of 2, 3 and 5 W for one minute duration a mild thermal injury was seen on microscopy (FIG. 2). When the duration of 5 W application was increased to 2 minutes a moderate thermal injury was observed with complete denudation of the biliary epithelium (FIG. 3). With the higher power setting of 10 W or greater, the thermal injury became evident at laparotomy (FIG. 4) and complete coagulation of the common bile duct was produced preventing EndoHPB from being reintroduced and activated. On histological assessment severe thermal changes with extensive and complete coagulative necrosis of the bile duct wall was demonstrated (FIG. 5).

TABLE 1

| | CBD diameter (mm) | Power (watts) | Heating Time (minutes) | Thermal Injury |
|---|---|---|---|---|
| Pig 1 | 25 | 2 | 1 | mild |
| | | 3 | 1 | mild |
| Pig 2 | 26 | 5 | 1 | mild |
| | | 5 | 2 | moderate |
| Pig 3 | 25 | 10 | 1 | severe |
| | | 20 | 1 | severe |

Conclusion

This work has established that EndoHPB handles well and is compatible with use via a side viewing endoscope through a 3.2 mm biopsy channel. In the context of a normal porcine bile duct the ideal power setting appeared to be about 5 W for around 2 minutes. When significantly higher power settings were used problems with reinsertion and application of EndoHPB into the common bile duct were encountered. Additionally, a more extensive thermal injury was produced macroscopically and microscopically which could correlate with the later development of bile leak, bowel perforation or pancreatitis.

Example 2

Background

The goal of this animal-based investigation was to examine the ability of RF energy to ablate and coagulate the tissues until induction of perforation. In this way the maximum parameters for thermal ablation can be determined.

Method

Ten mini pigs underwent general anesthesia. A side viewing endoscope (Fujinon Inc., NJ) was advanced through the mouth into the esophagus where a 10 French wire guide RF probe (Habib EndoHPB, EMcision™, UK) was placed in the upper esophagus to apply one watt (1 W) of energy for one minute, then advanced to the mid-esophagus to apply three watts (3 W) for 2 minutes, and finally, to the lower esophagus, where 5 watts (5 W) was applied for one minute. Five of the 10 animals were then sacrificed and the esophagus harvested by a dedicated veterinarian and surgeon to confirm the presence or absence of perforation. The five other pigs were kept alive for another month and remained healthy. Under general anesthesia, a repeat procedure was then performed using 50 W for 5 minutes, 30 W for 3 minutes until perforation was obtained and confirmed endoscopically and macroscopically Results On both gross and endoscopic examination of the esophagus, no perforation was noted using the low power settings (i.e. 1 to 5 W). The area where energy was applied appeared paler than the surrounding tissues indicating the ability to coagulate the areas to which the energy is applied and sparing the neighboring areas. Using high power settings (i.e.: 30 or 50 W) leads to perforation within only a few minutes of application.

Conclusions

The RFA device can provide enough controlled energy through the endoscope to induce tissue coagulation and ablation without inducing perforation when used at low wattage power settings. Its ability to be advanced over a wire and offer different levels of energy constitutes a tremendous potential for palliation of intraluminal cancerous obstruction.

Example 3

Background

Patients with un-resectable pancreatic or bile duct cancer were recruited. Exclusion criteria were: uncorrected coagulopathy, cardiac pacemaker, failure to insert guide-wire across biliary stricture, Karnofsky score less than 40% (Karnofsky, D. A., Abelmann W H, Craver L F, Burchenal J H, The use of the nitrogen mustards in the palliative treatment of carcinoma. With particular reference to bronchogenic carcinoma. Cancer, 1948. 1(4): p. 634-656) and inability to give informed consent. Prospective data was collected detailing ERCP complications, patient survival and stent patency up to 90 days post procedure, with serial liver function tests (and imaging where indicated) used to determine post ERCP biliary obstruction.

Intervention

Study ERCP with radiofrequency ablation (RFA) catheter was performed by experienced pancreatobiliary endoscopists. ERCP was performed under standard operating conditions with Olympus TJF-260 duodenoscopes (Olympus UK, Essex, UK). Previously placed plastic stents were removed prior to study cholangiography which then confirmed biliary stricture length and position. The RFA catheter was placed under fluoroscopic guidance across the biliary stricture, see FIG. 7(b).

The Habib™ EndoHPB (EMcision, UK) catheter used in this Example has FDA (USA Food and Drug Administration) and CE approval (European Union European Conformity). It is a bipolar RFA probe that is 8 Fr (2.6 mm), 1.8 m long, compatible with standard (3.2 mm working channel) side viewing endoscopes and passes over 0.035" guide wires. The catheter has 2 ring electrodes 8 mm apart with the distal electrode 5 mm from the leading edge providing local coagulative necrosis over a 2.5 cm length, FIG. 1.

Energy was delivered by an RFA generator (1500 RF generator, Rita Medical Inc, USA) delivering electrical energy at 400 kHz at 7-10 W for 2 minutes with a rest period of 1 minute prior to moving the catheter. Depending on the length of the stricture sequential applications were applied to ensure RFA treatment throughout the length of the stricture without significant overlap of treated areas. After RFA treatment uncovered SEMS (Wallstent, Boston Scientific, USA) were deployed as per standard protocols.

Trial Design

The design was a single centre open label pilot study to demonstrate safety and efficacy.

Results 22 patients were recruited to this pilot study between January 2009 and April 2010. Patient data is shown in Table 2. In one patient irretrievable proximal migration of a plastic stent resulted in no attempt to deploy the RFA catheter; a standard SEMS procedure was undertaken. SEMS placement was achieved in all cases of EndoHPB deployment. There were no technical difficulties placing the RFA catheter across the biliary stricture. Six study subjects had evidence of hepatic hilar or intra hepatic involvement. Three of these subjects underwent balloon dilatation of the stricture to facilitate further instrumentation. No attempt was made to place multiple SEMS in these patients at study ERCP. Asymptomatic biochemical pancreatitis (amylase 1450 U/l) developed post-ERCP in only one patient. Two patients developed cholecystitis requiring cholecystostomy; both these patients had tumour encasement of the cystic duct on abdominal CT scan and pre ERCP sepsis. One patient developed rigors post ERCP that settled after empiric antibiotic therapy. One patient did not demonstrate biliary decompression; subsequent review concluded there was significant intra-hepatic sub segmental biliary malignancy precluding successful biliary decompression.

30 day patency was maintained in all other patients with no 30 day mortality. At 90 day follow up the patient who failed to demonstrate biliary decompression had died, one further patient had died of disease progression with stent patent. Three other patients had developed biliary obstruction. Further RFA procedure data is summarised in Table 3.

Discussion

This trial represents a phase 1 study of endobiliary RFA treatment of malignant biliary obstruction and clearly demonstrates immediate and 30 day safety and 90 day efficacy.

Potential complications that were identified in pre-clinical animal models (such as in Examples 1 and 2) included extension of the RFA burn into local structures and difficulty reintroducing catheters into the bile duct after RFA treatment, but these complications were not apparent in the patients treated in this trial. Haemorrhage and abscess formation at the site of RFA, which are recognised complications of hepatic RFA did not occur in this study population (Mulier, S., et al., Radiofrequency ablation versus resection for resectable colorectal liver metastases: time for a randomized trial? An update. Dig Surg, 2008. 25(6): p. 445-60).

This is the first reported use of endo-biliary RFA and the reported complications in this pilot study are in keeping with literature reported type and incidence for biliary SEMS (Loew, B. J., et al., Comparative performance of uncoated, self expanding metal biliary stents of different designs in 2 diameters: final results of an international multicenter, randomized, controlled trial. Gastrointest Endosc, 2009. 70(3): p. 445-53).

Application of RFA within the bile duct induces local coagulative necrosis. RFA coagulative necrosis within a malignant biliary stricture will likely result in some damage to adjacent healthy bile duct, however, the use of two electrodes means that the heating pattern is substantially cylindrical and is stretched between the two electrodes. In this way the energy is spread over a larger volume than with a single electrode, and the spatial variation of energy deposition is less. In any case since the RFA burn was immediately followed by insertion of SEMS any potential biliary injury was empirically treated. Prospective data to determine the best treatment of bile duct injury in this situation is lacking, however with traumatic or surgical bile duct injuries endoscopic biliary stent placement is considered the best form of therapy (de Reuver, P. R., et al., Endoscopic treatment of post-surgical bile duct injuries: long term outcome and predictors of success. Gut, 2007. 56(11): p. 1599-605). There were no complications that could be attributed to full thickness bile duct RFA, nor was there any evidence of biliary leak during the 30 day follow up period.

This trial demonstrates 30 day safety and 90 day efficacy in human patients of the described disclosure.

TABLE 2

| Demographics | N = 22 |
|---|---|
| Sex: | male 11 |
| Age mean/range years | 70 (56-84) |
| Pancreatic/cholangiocarcinoma | 16/6 |
| Metastatic | N = 10 |
| Locally advanced | N = 17 |
| Metastatic and locally advanced | N = 7 |
| Declined surgery | N = 2 |
| Hilar stricture | N = 6 |
| Plastic stent prior to SEMS | N = 16 |
| Sepsis at RFA ERCP | N = 7 |
| Bilirubin median/range, μmol/l | 26 (4-286) |
| Karnofsky score median/range | 55 (40-100) |

TABLE 3

| RFA Procedure details | N = 21 |
|---|---|
| Procedure time, mean/range, minutes | 43 (22-68) |
| Fluoroscopic screening time, median/range, minutes | 5 (3-36) |
| Number of applications, median/range | 2 (1-4) |
| Total energy delivered, mean/range, Joules | 2474 (1200-3600) |
| Stricture diameter pre RFA, median/range, mm | 0 (0-1) |
| Stricture diameter post RFA, median/range, mm | 4 (3-6) |
| Length of stricture, mean/range, mm | 37 (20-60) |
| Post ERCP day stay, median/range, days | 1 (1-24) |
| Patients alive with biliary patency at 90 days (%) | 16/21 (76%) |

According to some exemplary implementations, the components of devices disclosed herein may be provided in any combination to accomplish desired functionality. Likewise, operations of methods disclosed may be provided in any sequence or combination to achieve results as disclosed herein.

While the method and agent have been described in terms of what are presently considered to be the most practical and preferred exemplary implementations, it is to be understood that the disclosure need not be limited to the disclosed exemplary implementations. It is intended to cover various modifications and similar arrangements included within the spirit and scope of the claims, the scope of which should be accorded the broadest interpretation so as to encompass all such modifications and similar structures. The present disclosure includes any and all exemplary implementations of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an exemplary implementation of any apparatus implementation, a method or process implementation, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular exemplary implementation, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative exemplary implementations.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A method for treating a duct of a patient, comprising:
directly visualizing an obstruction within the duct;
positioning a guidewire within the duct adjacent to, through or alongside the obstruction;
positioning a catheter within the duct adjacent to, through or alongside the obstruction, the catheter comprising:
a proximal end;
a distal end, wherein the distal end includes a distal tip portion; and
a pair of bipolar electrodes arranged longitudinally about the distal tip portion;
activating the pair of bipolar electrodes for a time and at a power sufficient to form a substantially cylindrical ablation volume along the pair of bipolar electrodes and reduce the extent of the obstruction;
wherein the time is about 90 seconds and the power is about 10 watts.

2. The method of claim 1, wherein the activating the bipolar electrodes step further comprises reestablishing normal patency of the duct.

3. The method of claim 1, wherein the obstruction is a complete blockage of the duct.

4. The method of claim 1, wherein the positioning a guidewire step positions the guidewire through the obstruction.

5. The method of claim 1, further comprising translating the catheter proximally to a second position along the obstruction after the activating step and re-activating the bipolar electrodes at the second position.

6. The method of claim 1, further comprising at least partially dilating the duct with an expanding member along the obstruction.

7. The method of claim 1, wherein the directly visualizing step is performed both before and after the activating step.

8. The method of claim 1, wherein a distal electrode of the pair of bipolar electrodes is positioned a distance from the distal tip portion of the catheter.

9. The method of claim 8, wherein the distance is about 5 millimeters.

10. The method of claim 1, further comprising:
inserting a balloon within the duct prior to or after the activating step; and
expanding the balloon sufficiently to at least partially dilate the duct at the obstruction.

11. The method of claim 1, wherein the duct is selected from the group consisting of a biliary duct, a pancreatic duct, and a urinary duct.

12. A method for treating a duct of a patient comprising:
positioning a catheter adjacent to, through or alongside an obstruction within the duct, the catheter comprising:
a proximal end;
a distal end, wherein the distal end includes a distal tip portion;
a pair of bipolar electrodes arranged longitudinally about the distal tip portion, wherein a longitudinal length of each electrode of the pair of bipolar electrodes is at least as great as a longitudinal spacing between the electrodes of the pair of bipolar electrodes; and activating the pair of bipolar electrodes for a time and at a power sufficient to reduce the extent of the obstruction;

wherein the time is about 90 seconds and the power is about 10 watts.

13. The method of claim 12, further comprising directly visualizing the obstruction.

14. The method of claim 12, further comprising dilating the duct prior to or after the activating step.

15. The method of claim 12, wherein the duct is selected from the group consisting of a biliary duct, a pancreatic duct, and a urinary duct.

16. A method for treating an at least partially obstructed stent comprising:

positioning a catheter within a biliary duct and within at least a portion of the stent, and adjacent to, through or alongside the obstruction, the catheter comprising:
 a proximal end;
 a distal end, wherein the distal end includes a distal tip portion;
 a pair of bipolar electrodes arranged longitudinally about the distal tip portion; and activating the pair of bipolar electrodes for a time and at a power sufficient to reduce the extent of the obstruction;

wherein the time is about 90 seconds and the power is about 10 watts.

17. The method of claim 16, further comprising directly visualizing the obstruction.

18. The method of claim 16, further comprising cannulating the portion of the stent.

\* \* \* \* \*